United States Patent

Hodorek et al.

Patent Number: 5,916,221
Date of Patent: Jun. 29, 1999

[54] NOTCH/CHAMFER GUIDE

[75] Inventors: Robert A. Hodorek, Warsaw, Ind.; John N. Insall, New York, N.Y.

[73] Assignee: Bristol-Myers Squibb Company, New York, N.Y.

[21] Appl. No.: 08/931,976

[22] Filed: Sep. 17, 1997

[51] Int. Cl.$^6$ .................................................. A61B 17/56
[52] U.S. Cl. .................. 606/89; 606/88; 83/745
[58] Field of Search .................. 606/89, 88, 87; 83/745

[56] References Cited

U.S. PATENT DOCUMENTS

| | | | |
|---|---|---|---|
| 4,721,104 | 1/1988 | Kaufman et al. | 128/92 VW |
| 5,035,699 | 7/1991 | Coates | 606/86 |
| 5,098,436 | 3/1992 | Ferrante et al. | 606/88 |
| 5,405,349 | 4/1995 | Burkinshaw et al. | 606/88 |
| 5,417,694 | 5/1995 | Marik et al. | 606/88 |
| 5,454,816 | 10/1995 | Ashby | 606/88 |
| 5,514,139 | 5/1996 | Goldstein et al. | 606/88 |
| 5,569,259 | 10/1996 | Ferrante et al. | 606/87 |
| 5,569,261 | 10/1996 | Marik et al. | 606/88 |
| 5,593,411 | 1/1997 | Stalcup et al. | 606/89 |
| 5,688,279 | 11/1997 | McNulty et al. | 606/88 |
| 5,735,856 | 4/1998 | McCue et al. | 606/88 |

OTHER PUBLICATIONS

Insall/Burstein II—Modular Knee System Brochure "Simple, Precise Instrumentation"—Zimmer, Inc. c1993.

*Primary Examiner*—M. Rachuba
*Assistant Examiner*—Stephen Choi
*Attorney, Agent, or Firm*—Cary R. Reeves

[57] ABSTRACT

A notch/chamfer guide has chamfer and trochlear recess cutting slots and a notch, corresponding to the intercondylar box of a femoral implant, with a removable notch slot attachment. With the notch slot attachment assembled to the cutting guide adjacent the notch, blade receiving slots are defined between the notch slot attachment and the inside walls of the notch. The slots provide control to the saw blade to prevent the blade from angling away from the notch walls and making imprecise cuts. The notch slot attachment is removable to allow easy access to the notch area so that a manual instrument such as an osteotome can be used for final removal of the notch bone and to facilitate the use of an oscillating saw in the chamfer slots of the guide. A U-shaped notch is provided for cutting a trochlear recess that will lie behind the anterior portion of the implanted knee component to receive the backside of the patellar track of the implant. The outside surface of the guide, corresponding to the distal aspect of the femur, is angled so that it is parallel to the guide surface which guides the cut forming the top of the intercondylar notch. This parallel external surface of the guide acts as a visual reference such that when a saw blade being used to cut the sides of the intercondylar notch is held perpendicular to the external surface it will intersect at a right angle the cut forming the top of the intercondylar notch.

5 Claims, 3 Drawing Sheets

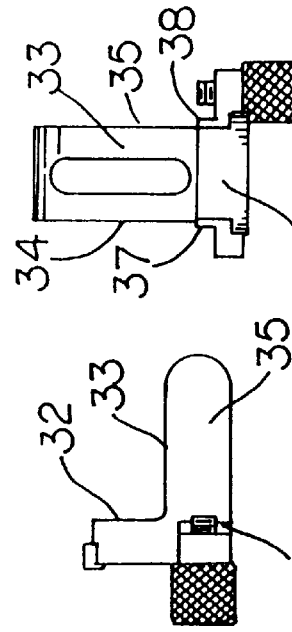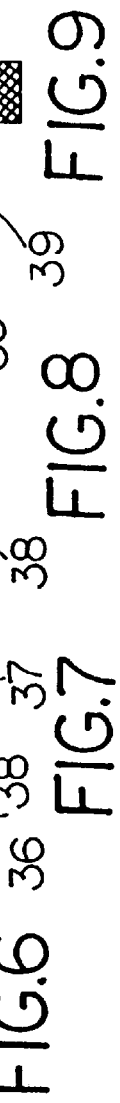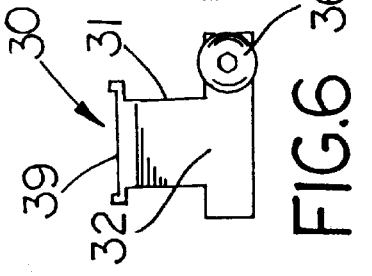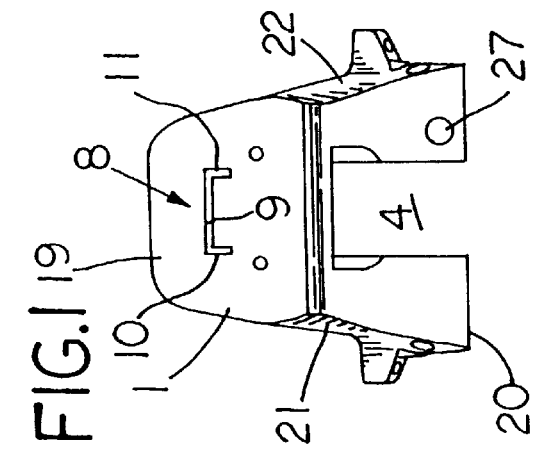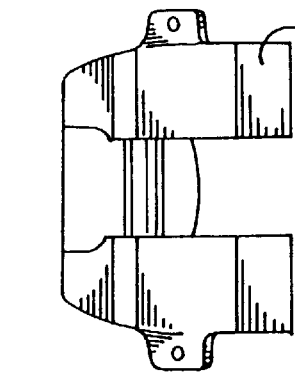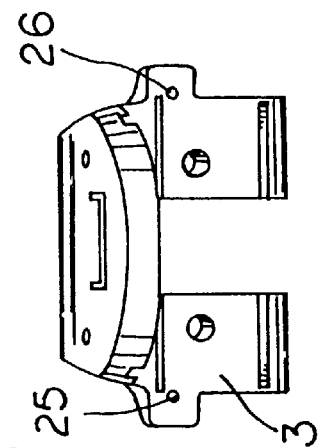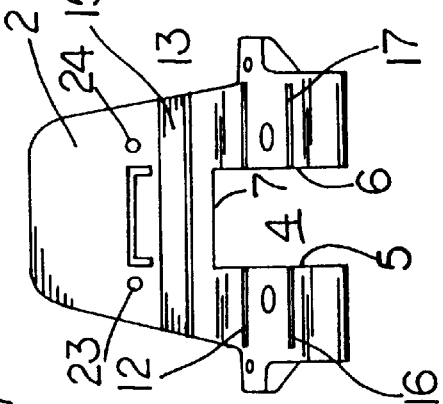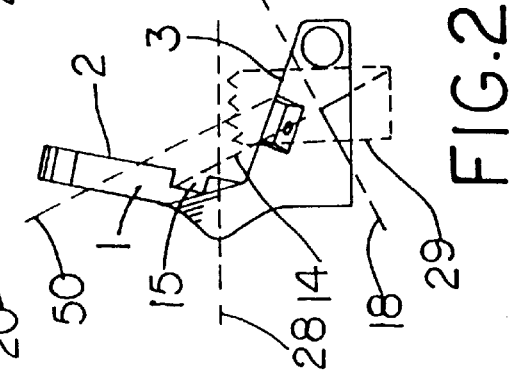

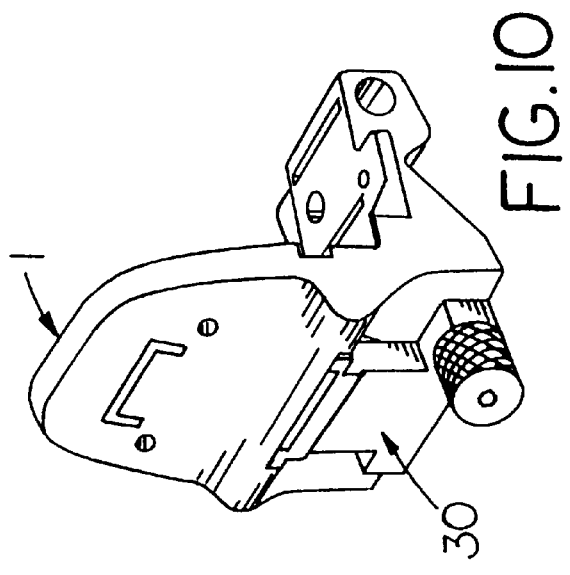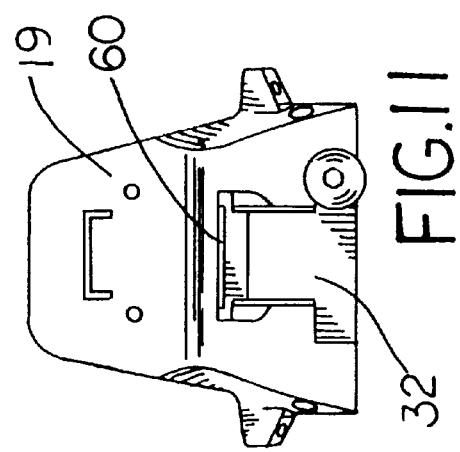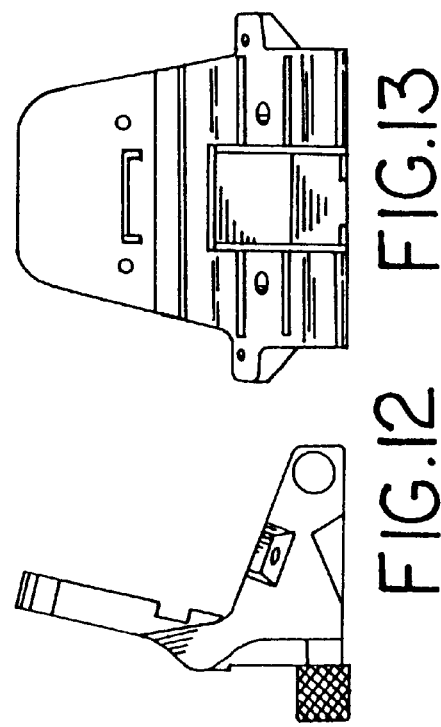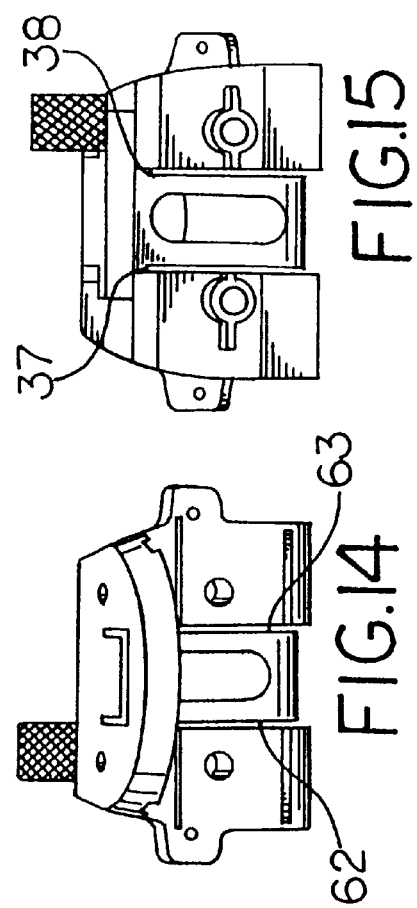

NOTCH/CHAMFER GUIDE

BACKGROUND OF THE INVENTION

The present invention relates to cutting guides for knee replacement surgery. More particularly, the present invention relates to a notch/chamfer guide for final cutting of the femoral bone, forming an intercondylar notch, and forming a trochlear recess.

During the course of a knee replacement surgery, the femoral bone must be cut to fit the internal shape of the femoral implant. A cutting guide is generally provided for guiding a saw blade in making the cuts. In the case of a femoral implant that includes a raised internal box, the cutting guide includes a notch corresponding to the box shape. To produce the box cut in the bone, a saw blade is held against the side of the guide notch and directed into the bone.

SUMMARY OF THE INVENTION

The present invention improves on the prior cutting guides by providing a notch/chamfer guide having chamfer and trochlear recess cutting slots and a notch, corresponding to the intercondylar box of a femoral implant, with a removable notch slot attachment. With the notch slot attachment assembled to the cutting guide adjacent the notch, blade receiving slots are defined between the notch slot attachment and the inside walls of the notch. The slots provide better control to the saw blade to prevent the blade from angling away from the notch walls and making imprecise cuts. The notch slot attachment is removable to allow easy access to the notch area so that a manual instrument such as an osteotome can be used for final removal of the notch bone. Removal of the notch slot attachment also makes it easier to use an oscillating saw in the chamfer slots of the guide. A U-shaped notch is provided for cutting a trochlear recess that will lie behind the anterior portion of the implanted knee component to receive the backside of the patellar track of the implant. The anterior inside surface of the cutting guide includes a channel for receiving a saw blade tip when cutting the anterior chamfer so that the blade extends beyond the surface of the bone and the chamfer bone is cut free from the femur. Finally, the outside surface of the guide, corresponding to the distal aspect of the femur, is angled so that it is parallel to the guide surface which guides the cut forming the top of the intercondylar notch. This parallel external surface of the guide acts as a visual reference such that when a saw blade being used to cut the sides of the intercondylar notch is held perpendicular to the external surface it will intersect at a right angle the cut forming the top of the intercondylar notch. This eliminates unnecessarily deep cutting of the bone which occurs when a saw blade is repeatedly extended by feel into the notch along its sides at an unknown angle to intersect the other cuts.

BRIEF DESCRIPTION OF THE DRAWINGS

FIG. 1 is a front perspective view of a notch/chamfer guide according to the present invention.

FIG. 2 is a side perspective view of the notch/chamfer guide of FIG. 1.

FIG. 3 is a rear perspective view of the notch/chamfer guide of FIG. 1.

FIG. 4 is a top perspective view of the notch/chamfer guide of FIG. 1.

FIG. 5 is a bottom perspective view of the notch/chamfer guide of FIG. 1.

FIG. 6 is a front perspective view of a notch slot attachment according to the present invention.

FIG. 7 is a rear perspective view of the notch slot attachment of FIG. 6.

FIG. 8 is a side perspective view of the notch slot attachment of FIG. 6.

FIG. 9 is a top perspective view of the notch slot attachment of FIG. 6.

FIG. 10 is an isometric view of an assembly of the notch/chamfer guide of FIG. 1 and the notch slot attachment of FIG. 6.

FIG. 11 is a front perspective view of the assembly of FIG. 10.

FIG. 12 is a side perspective view of the assembly of FIG. 10.

FIG. 13 is a rear perspective view of the assembly of FIG. 10.

FIG. 14 is a top perspective view of the assembly of FIG. 10.

FIG. 15 is a bottom perspective view of the assembly of FIG. 10.

DETAILED DESCRIPTION OF THE INVENTION

Figure 18:
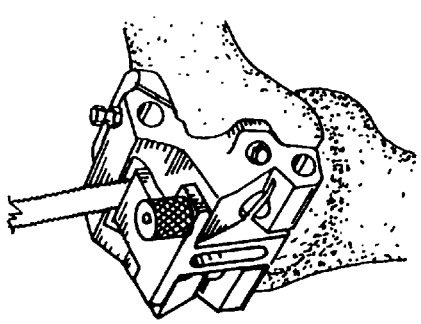
FIGS. 16–21 are isometric views of the notch/chamfer guide of FIG. 1 and the notch slot attachment of FIG. 6 being used to cut a distal femur.

FIGS. 1–5 depict an exemplary notch/chamfer guide according to the present invention. The guide includes a guide body 1 defining a generally L-shaped angular block. The inside of the guide includes an anterior surface 2 and a distal surface 3. A notch 4 extends from the distal surface 3 through the guide 1. The notch 4 is bordered by side walls 5 and 6 and a top wall 7. The top wall 7 forms a plane angled away from the distal surface 3 so that a saw blade 28 placed flat against the top wall 7 is angled away from the distal surface 3 in a plane corresponding to the top of an intercondylar relief notch to be formed in the femoral bone, as shown in hidden lines in FIG. 2. A saw blade 29 placed flat against the side walls 5 and 6 in turn is guided to form the sides of the interchondylar relief notch.

Several slots extend through the guide and form openings in the anterior and distal surfaces. A U-shaped slot 8 passes through the anterior surface 2. The U-shaped slot has a base portion 9 and sides 10 and 11. The U-shaped slot 8 is angled so that a saw blade 50 placed in the slot forms an acute angle with the anterior and distal surfaces 2 and 3, as shown with hidden lines in FIG. 2. The angle of the U-shaped slot corresponds to the angle of a trochlear eminence on a femoral component. A saw blade activated in the base portion 9 and sides 10 and 11 of the U-shaped slot cuts a piece of bone from the femur thus leaving a trochlear recess shaped to receive the trochlear eminence of the implant.

Anterior chamfer slots 12 and 13 pass through the distal surface 3. The anterior chamfer slots are angled so that a saw blade 14 placed in the slots forms an acute angle with the anterior and distal surfaces 2 and 3, as shown with hidden lines in FIG. 2. These slots guide a saw blade to remove an anterior chamfer, or corner, from the distal femur corresponding to an anterior chamfer of a femoral implant. A channel 15 is cut into the anterior surface 2 opposite the anterior slots 12 and 13. The channel 15 receives the tip of the saw blade 14 so that the saw cuts entirely through the femoral bone anteriorly.

Posterior chamfer slots 16 and 17 also pass through the distal surface 3. The posterior chamfer slots are angled so that a saw blade 18 placed in the slots forms an acute angle with the distal surface 3 and is directed away from the anterior surface 2, as shown in hidden lines in FIG. 2. These slots guide a saw blade to remove a posterior chamfer from the distal femur corresponding to a posterior chamfer of a femoral implant. Both the anterior 12 and 13 and distal 16 and 17 chamfer slots open interiorly into the notch 4 and are closed toward the sides of the guide. This allows the use of an oscillating saw blade in these slots without the possibility of the blade jumping out of the slots toward the outside of the guide and potentially injuring surrounding tissues.

The exterior of the guide includes front 19 and bottom 20 surfaces opposing the anterior 2 and distal 3 interior surfaces respectively. The bottom surface 20 defines a reference plane parallel to the notch top surface 7. Thus, when a saw blade 29 is held against either of the side walls 5 and 6 and is oriented pependicularly to the bottom surface 20, the saw blade 29 will intersect the plane of the notch top surface 7 at a right angle. This provides a visual reference to a surgeon to allow him to cut only as deeply as is necessary to complete the intercondylar notch side cuts. Side surfaces 21 and 22 oppose the interior side walls 5 and 6. The guide also includes anterior fixation holes 23–24 and distal fixation holes 25 and 26 that receive fixation pins that extend through the guide to attach it to the distal femur. A threaded hole 27 is formed in the front surface of the guide.

FIGS. 6–9 depict a notch slot attachment 30 for use with the guide of FIGS. 1–5. The notch slot attachment includes an L-shaped angular body 31. One leg of the L forms an anterior portion 32 of the attachment and the other leg forms a distal portion 33 of the attachment. The top 39 of the anterior portion 32 is a flat blade guiding surface corresponding to the top of the intercondylar notch to be formed in the femur. The sides 34 and 35 of the distal portion are flat blade guiding surfaces corresponding to the sides of the intercondylar notch to be formed in the femur. A coupling screw 36 is mounted on the anterior portion 32 of the attachment 30. Shoulders 37 and 38 project from the sides 34 and 35 of the distal portion adjacent the anterior portion 32.

FIGS. 10–15 depict the notch slot attachment 30 of FIGS. 6–9 assembled to the notch/chamfer guide 1 of FIGS. 1–5. To assemble the two parts, the notch slot attachment 30 is placed inside of the notch 4 with the anterior portion 32 aligned with the front 19 of the notch/chamfer guide and the distal portion 33 aligned with the bottom 20 of the notch/chamfer guide. The coupling screw 36 is tightened to hold the attachment 30 firmly against the guide 1. The shoulders 37 and 38 abut the sides of the notch and thus prevent the attachment 30 from rocking or rotating relative to the guide 1.

When the two parts are assembled, the top 39 of the anterior portion 32 of the attachment and the top surface 7 of the notch 4 bound a slot 60 that receives a blade in close fit relationship so that the blade is held parallel to the top surface 7 of the notch. Likewise, the sides 34 and 35 of the distal portion 33 and the side walls 5 and 6 of the notch 4 bound slots 62 and 63 that receive a blade in close fit relationship so that the blade is held parallel to the side walls 5 and 6.

Figure 21:
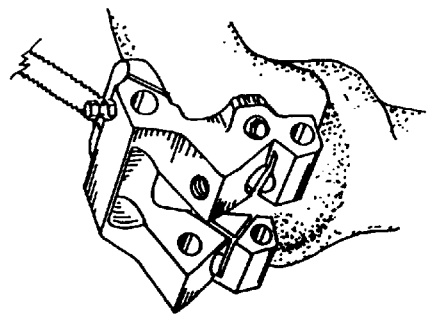
Figure 17:
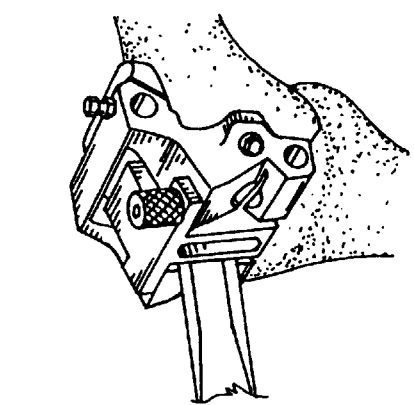
Figure 20:
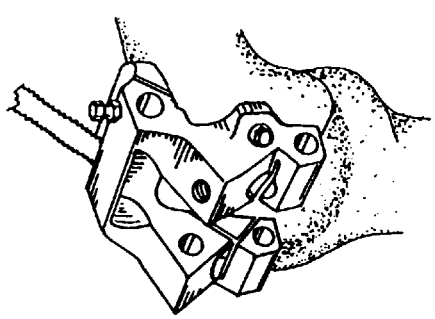
Figure 16:
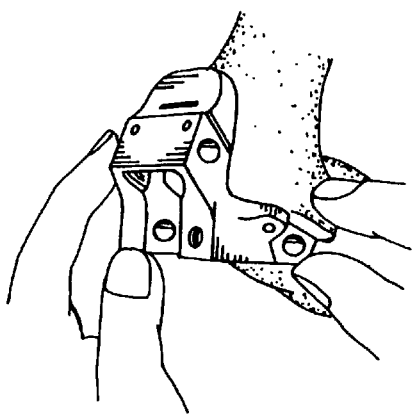
Figure 19:
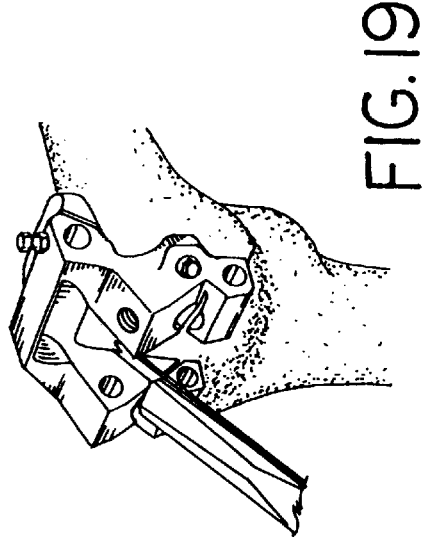

FIGS. 16–21 depict the use of the notch/chamfer guide. The guide 1 is placed on the distal femur after initial anterior and distal cuts have been made. The guide is fixed in place with pins placed through the fixation holes 23, 24, 25, and 26. The notch slot attachment 30 is assembled to the guide 1. The intercondylar notch cuts are made by activating saw blades in the notch blade slots 60, 62 and 63. In making the notch side cuts through the side slots 62 and 63, the blade is visually aligned so that it is parallel with the bottom surface 20 of the guide so that the blade will intersect the cut made through slot 60 at right angles and complete the notch cut without unnecessarily deep cutting along the sides.

After the box cuts are completed, the notch slot attachment is removed. With the notch slot attachment out of the way, an osteotome can be used to complete the removal of the notch bone in necessary. Next, the chamfer cuts are made. With the notch slot attachment out of the way, a saw blade has sufficient room to reciprocate in making the chamfer cuts. Finally, the trochlear recess is cut by activating saw blades in the sides 10 and 11 and base portion 9 of the U-shaped slot 8, thus completing all of the femoral finishing cuts.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A cutting guide for guiding a saw blade to cut a distal femur to receive a femoral implant comprising;

a cutting guide for guiding a saw blade comprising an L-shaped body having interior and exterior surfaces, the interior surface including a first interior surface angled relative to a second interior surface, the first interior surface including a notch extending from the first interior surface through the cutting guide, the notch being bordered by first and second side walls and a top wall, the first and second side walls and the top wall being flat, blade guiding surfaces;

a notch slot attachment comprising an L-shaped body having first and second members forming the L-shaped body, the first member having first and second sides and the second member having a top, the sides of the first member and the top of the second member being flat, blade guiding surfaces, the notch slot attachment being mounted within the notch of the cutting guide with the first side of the first member near the first notch side wall thus defining a saw blade slot between them, the second side of the first member near the second notch side wall thus defining a saw blade slot and the top of the second member being near the notch top wall, thus defining a saw blade slot between them; and means for removably securing the notch slot attachment within the notch of the cutting guide.

2. The cutting guide of claim 1 wherein the second interior surface further includes a U-shaped slot extending from the second interior surface through the cutting guide.

3. The cutting guide of claim 2 wherein the first interior surface further includes anterior and posterior chamfer slots extending from the first surface through the cutting guide, the anterior chamfer slots guiding a saw blade from the exterior of the guide toward the second interior surface.

4. The cutting guide of claim 3 wherein the second interior surface includes a channel cut into the surface and located to receive the tip of a saw blade guided by the anterior chamfer slots.

5. The cutting guide of claim 1 wherein the exterior surfaces of the guide include a bottom surface, the bottom surface opposing the first interior surface, the bottom surface defining a reference plane parallel to the notch top wall so that when a saw blade is held against either of the first and second notch side walls and the saw blade is oriented perpendicular to the bottom surface, the saw blade will be perpendicular to the notch top wall.

\* \* \* \* \*